United States Patent [19]

Jönsson

[11] 4,089,957

[45] May 16, 1978

[54] THERAPEUTIC COMPOSITIONS AGAINST RECURRENT THROMBOSIS

[75] Inventor: Nils Ake Jönsson, Solna, Sweden

[73] Assignee: AB Kabi, Stockholm, Sweden

[21] Appl. No.: 803,876

[22] Filed: Jun. 6, 1977

[30] Foreign Application Priority Data

Jun. 11, 1976 Sweden .................................. 7606632

[51] Int. Cl.$^2$ ............................................ A61K 31/535
[52] U.S. Cl. .................................................. 424/248.56
[58] Field of Search ................................... 424/248.56

[56] References Cited
PUBLICATIONS

Chem. Abst., 8th Collective Index, vol. 66–75 (1967–1971), p. 19777s.

Primary Examiner—Sam Rosen
Attorney, Agent, or Firm—A. A. Orlinger

[57] ABSTRACT

Disclosed is (1) a method of resisting as well as suppressing recurrent venous thrombosis in a human susceptible to or having said thrombosis, which method comprises administering to said human a recurrent venous thrombosis-combatting effective dose of a pharmaceutical composition comprising a pharmaceutically acceptable acid addition salt of moroxydine, such as of an inorganic acid as hydrochloric or sulphuric, or an aliphatic carboxylic acid such as any of acetic, ascorbic, citric, fumaric, gluconic, glycolic, lactic, levulinic, maleic, tartaric, salicylic or nicotinic acids, and (2) pharmaceutical preparations containing such acid addition salts for the indicated use.

8 Claims, No Drawings

THERAPEUTIC COMPOSITIONS AGAINST RECURRENT THROMBOSIS

This invention is that of a pharmaceutical composition comprising a physiologically acceptable acid addition salt of $N^1$, $N^1$-anhydrobis-(beta-hydroxyethyl)-biguanide (briefly referred to herein by its generic name moroxydine) and effective in combatting (i.e. the prevention and treatment of) recurrent venous thrombosis (i.e. RVT).

The invention is also that of the method of combatting RVT in humans, which method comprises administering to a subject susceptible to, or a patient suffering from, RVT a prophylactically or therapeutically effective dosage of a composition comprising a pharmaceutically acceptable acid addition salt of moroxydine.

As described by Inga Marie Nilsson et al. in Acta Med. Scand. Vol. 198 (1975) pp. 107–113 and in Progress in Chem Fibrinolysis and Thrombolysis Vol. 7 (1975) pp. 1–12, Raven Press, New York, N.Y., patients with recurrent idiopathic venous thrombosis have a decreased level of the plasminogen activator in the vein walls and/or a defective release mechanism for the activator from the vein walls. Corrective treatment of RVT has involved injections of insulin, oral administration of a blood sugar lowering sulfonamide or a blood sugar lowering biguanide, N -phenethyl-biguanide (phenformin) alone or combined with ethylestrenol.

The laboratory methods used for the objective assessment of the therapeutic effect are described by Nilsson (loc.cit.).

Patients suffering from RVT need a continued prophylactic medication to prevent thrombosis occurrence, and long term administration of blood sugar lowering drugs are considered a drawback because of the potential risks involved. Phenformin in addition causes a rare but serious side effect as well in diabetics given the drug for blood sugar reduction as in patients with RVT given the drug for prophylaxis, this side effect being lactic acidosis, as described by P. H. Wise et al. in Brit. Med. J. (January 10, 1976), pp. 70–72.

Against the given background for the development of drug treatment in the prophylaxis of RVT, it is most surprising that moroxydine which is devoid of any blood sugar lowering effect whatsoever, nevertheless manifests a stimulatory effect on the plasminogen activator of the vein walls to enable a beneficial effect in the prevention of RVT.

The pharmaceutical compositions of the invention are effective when administered orally or parenterally. For clinical prophylactic use in humans, dosage forms for oral administration are advantageous.

The effective agent in the composition of the invention is a physiologically acceptable acid addition salt of moroxydine, e.g. the hydrochloride, according to the following formula

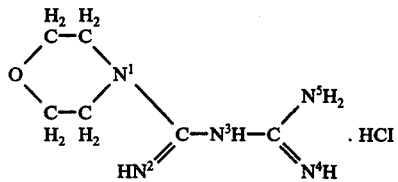

Other physiologically acceptable acid addition salts of moroxydine applicable in the composition of this invention are, e.g. the sulfate, aliphatic acid salt such as of a mono-, di- or tricarboxylic acid, as the acetate, ascorbate, citrate, fumarate, lactate, maleate, succinate, or of an aromatic carboxylic acid as the salicylate, or of a heterocyclic carboxylic acid as the nicotinate, or of an aliphatic hydroxy acid as the gluconate or glycolate.

The moroxydine hydrochloride used in the composition according to the invention is prepared, i.e. as follows:

43.5 g. tetrahydro-1,4-oxazine, 41.7 ml. concentrated hydrochloric acid, 40 ml. water, and 43 g. dicyandiamide are refluxed for 48 hours, whereafter the reaction mixture is cooled to + 5° C. and filtered. The filtrate is evaporated to dryness and extracted with boiling ethanol. Yield: 50 g. The formed moroxydine-HCl is purified by recrystallization from ethanol. M.P.: 210°–212° C.

Alternatively, the free base of moroxydine is prepared, e.g.: 2.1 g. moroxydine hydrochloride is dissolved in 100 ml. water and treated with an anion exchange resin. The resulting solution is neutralized, for example, with maleic acid and evaporated to crystallization yielding moroxydine maleate.

Thus, e.g., using each one separately of sulphuric acid, acetic acid, citric acid, fumaric acid, lactic acid, ascorbic acid, maleic acid, succinic acid, levulinic acid, salicylic acid and nicotinic acid respectively with moroxydine (i.e. as the base), there similarly is obtained separately respectively the corresponding acid addition salt of moroxydine. Each of these acid addition salts is considered as herein fully disclosed, i.e. starting with moroxydine sulphate, acetate, citrate and so correspondingly on to moroxydine nicotinate, moroxydine gluconate and moroxydine glycolate.

The various compositions according to the invention, comprising any selected such acid addition salt of moroxydine are used clinically, e.g., as the corresponding sterile aqueous solutions containing, say, from 102 to about 250 mg. of moroxydine per ml. Tablets, coated tablets, and capsules containing any such acid addition salt of moroxydine at from 102 to 1000 mg. per dosage until also are employed. Elixirs with the same basic moroxydine content as in sterile solutions also can be used. An effective dosage schedule covers a range from about 500 mg. to about 1000 mg. two times daily.

There thus is available a wide dosage range for administration of the various compositions of the invention. A practical range for administration of any of these acid addition salts of moroxydine is at from about 100 mg. to about 1000 mg. daily.

A series of 62 patients (38 female and 24 male) have received moroxydinic HCl orally at the dose level of 800 mg. (2 tablets of 400 mg. each) twice daily for a period varying among them of from 3 to 18 months. Objective improvement according to the parameters used was recorded in 47 of the 62 patients, corresponding to 75% of the cases. No RVT occurred during therapy and no side effects were observed. Serum transaminases, serum ceratinine, bilirubin and urea were checked for clinical chemistry. The blood sugar level was found to be normal at all times.

Details of the study are presented in the following table:

| Period of medication Months | No. of patients/group | Results | |
|---|---|---|---|
| | | Good effect | No effect |
| 3 | 11 | 9 | 2 |
| 4–6 | 18 | 13 | 5 |
| 7–9 | 15 | 10 | 5 |
| 10–12 | 7 | 6 | 1 |
| 13–15 | 9 | 7 | 2 |
| 16–18 | 2 | 2 | — |
| | 62 | 47 | 15. |

The following examples illustrate, but without limiting, the invention:

Example 1.

| Sterile solution, composition: | Gm. |
|---|---|
| Moroxydine-HCl | 100, |
| Sterile water (for injection) | 926. |

Preparation

The moroxydine hydrochloride was dissolved in the warm sterile, pyrogen free water. The resulting solution was passed through a pre-filter and membrane filter (having 0.22 micron pores), and aseptically subdivided into sterile ampuls having 10 ml. of the sterile filtered solution in each. The ampuls then were flame sealed, containing 100 mg. of moroxydine hydrochloride per ml.

Example 2.

| Tablets, composition: | Gms. |
|---|---|
| Moroxydine HCl | 400, |
| Wheat starch | 75, |
| Lactose | 65.5, and |
| Magnesium stearate | 4.5. |

Preparation

A granulation was prepared by mixing together the moroxydine hydrochloride, wheat starch and lactose, and granulating their mixture with incorporating into it a paste of 20 gms. of starch and 15 ml. of water. The resulting granulation was dried and the magnesium stearate was admixed with the dried granulation and the resulting mixture was compressed into 1000 tablets.

Example 3.

| Sugar coated tablets, composition: | Gms. |
|---|---|
| Moroxydine-HCl | 400, |
| Wheat starch | 75, |
| Lactose | 65.5, and |
| Magnesium stearate | 4.5. |

Preparation

A tablet granulation was prepared as described in Example 2 and compressed into cores in a concave punch.

The cores were coated in the customary manner with consecutive layers of aqueous sucrose solutions of the different concentrations varying between 67 and 50% of sucrose and finishing with the customary dusting powder consisting of sucrose and talc.

Example 4.

| Effervescent tablets, composition: | Gms. |
|---|---|
| Moroxydine-HCl | 400, |
| Tartaric acid | 296, |
| Sodium bicarbonate | 334, |
| Gelatin | 3.5, and |

Example 4.-continued

| Effervescent tablets, composition: | Gms. |
|---|---|
| Polyethylene glycol 6000 | 6.5. |

Preparation

The moroxydine-HCl was granulated with an aqueous solution of the gelatin and polyethylene glycol 6000 in 35 ml. of water. Each of the tartaric acid and sodium bicarbonate also was granulated separately with this solution. The three granulations then were dried, screened and mixed together. The mixed granulations were compressed into 1000 tablets.

EXAMPLE 5

Capsules, composition:

A mixture was prepared containing equal parts by weight of moroxydine-HCl and lactose.

Preparation

The mixture was filled at 400 mg. per capsule into standard clear gelatin telescopic capsules, and after closing the capsules preferably were dusted with talc or corn-starch. The resulting capsules contained per dosage unit 200 mg. of moroxydine-HCl each.

Example 6.

| Elixir, composition: | Gms. |
|---|---|
| Moroxydine-HCl | 10, |
| Sorbitol, 70% | 35, |
| Methylparaben | 0.1, |
| Citric acid | 0.2, |
| Cacao flavour | 0.002, |
| Peppermint oil | 0.002, |
| Alcohol, 95% | 5, and |
| Water to make 100 ml. | |

Preparation

The moroxydine-HCl and citric acid were dissolved in the water. The sorbitol was admixed in their solution. The flavouring agents and the methylparaben were dissolved in the alcohol and the resulting solution was admixed with the first solution.

While the therapeutic compositions of these several specific examples contain the moroxydine hydrochloride, that hydrochloride can be replaced in each of the examples in part or as a whole by the equivalent quantity as to moroxydine of any other therapeutically acceptable moroxydine hydrohalide or of some other pharmaceutically acceptable acid addition salt of moroxydine of the type broadly described herein above and particularly of any of them which is specially named wherein as well as the tartrate. Thus, each of these specific examples is to be considered as if it is repeated in full but with such an equivalent amount of each of these other specific acid addition salts of moroxydine respectively separately thus replacing its hydrochloride.

The composition of the invention is not limited to that of any such acid addition salt in the specific solid or liquid pharmaceutically acceptable vehicle of the respective individual example. The pharmaceutical composition of the invention thus includes any other solid or liquid pharmaceutically acceptable vehicle, the constitution of which (i) is compatible with the selected moroxydine acid addition salt and (ii) provokes no undesirable side effects in the dosage used over the required period of administration.

The method of the invention comprises administering to a subject susceptible to, or a patient suffering from, RVT a pharmaceutically acceptable acid addition salt of moroxydine, i.e., its hydrochloride, at a dosage, say, of from about 100 to about 1000 mg. daily. The hydrochloride, of course, can be replaced in this method by the moroxydine equivalent quantity of any other of its pharmaceutically acceptable acid addition salts.

Considered broadly, the method of the invention is that of resisting as well as suppressing recurrent venous thrombosis in a human susceptible to, or having such thrombosis, which method comprises administering to said human a recurrent venous thrombosis-combatting effective dose of a pharmaceutical composition comprising a pharmaceutically acceptable acid addition salt of moroxydine.

More specifically, the just foregoing method is such wherein the acid addition salt of moroxydine is its sulfate, a hydrohalide, that of a mono-, di-, or tricarboxylic acid, including the acetate, glycolate, levulinate, fumarate, maleate, succinate, or citrate, or of an aliphatic mono-, di-, tetra- or penta-hydroxy acid including the lactate, tartrate, ascorbate, or gluconate, or of an aromatic carboxylic acid as the salicylate, or of a heterocyclic carboxylic acid as the nicotinate.

Beneficially the foregoing method is that in which the acid addition salt is a hydrohalide and advantageously the hydrochloride.

A beneficial embodiment of the method of the invention is the just earlier above method wherein said acid addition salt is administered in a regimen of from about 500 mg. to about 1000 mg. twice daily.

Productwise, the invention is that of a pharmaceutical composition effective for the prophylaxis of, as well as suppressing, recurrent venous thrombosis in a human susceptible to or having said thrombosis, which preparation comprises a pharmaceutically acceptable acid addition salt of moroxydine in a pharmaceutically acceptable dosage form vehicle whereby said composition is in a pharmaceutically acceptable dosage form that contains per dose from at least more than 500 milligrams to about 1000 milligrams of said acid addition salt.

In said pharmaceutical preparation, the acid addition salt can be any of those identified in relation to the method of the invention and likewise that of any of the herein indicated inorganic acids or any of the likewise mentioned organic acids, and advantageously a halohydride and particularly the hydrochloride.

The expression "pharmaceutically acceptable" used herein and in the appended claims is the recognized equivalent for the expression "physiologically acceptable" or "physiologically innocuous" or "therapeutically acceptable" commonly used to designate a substance which is physiologically innocuous when taken in a regimen (i.e. frequency of administration) that is effective for its indicated therapeutic use.

While the invention has been illustrated by giving detailed descriptions of certain specific embodiments of it, it is understood that various modifications and/or substitutions can be made in any of the specific embodiments within the scope of the invention as broadly disclosed herein and of the appended claims which are intended also to cover equivalents of the various specific embodiments.

What is claimed is:

1. The method of resisting as well as suppressing recurrent venous thrombosis in a human susceptible to or having said thrombosis, which method comprises administering to said human a recurrent venous thrombosis-combatting effective dose of a pharmaceutical composition comprising a pharmaceutically acceptable acid addition salt of moroxydine.

2. The method as claimed in claim 1, wherein said acid addition salt is that of an inorganic acid.

3. The method as claimed in claim 2, wherein said acid addition salt is moroxydine hydrochloride.

4. The method as claimed in claim 1, wherein said acid addition salt is that of an aliphatic mono-, di-, or tricarboxylic acid.

5. The method as claimed in claim 4, wherein said aliphatic carboxylic acid is monohydroxy, dihydroxy, tetrahydroxy or pentahydroxy substituted.

6. The method as claimed in claim 1, wherein said acid addition salt is the hydrochloride, sulfate, acetate, ascorbate, citrate, fumarate, gluconate, glycolate, lactate, levulinate, maleate, tartrate, salicylate, or nicotinate.

7. The method as claimed in claim 1, wherein said effective dose in from 500 to about 1000 milligrams.

8. The method as claimed in claim 7, wherein said dose is administered more then twice daily.

* * * * *

UNITED STATES PATENT OFFICE
CERTIFICATE OF CORRECTION

Patent No. 4,089,957            Dated May 16, 1978

Inventor(s)     Nils Ake Jönsson

It is certified that error appears in the above-identified patent and that said Letters Patent are hereby corrected as shown below:

Column 6, line 44, claim 7 line 2, "in" should read -- is --.

Signed and Sealed this

Seventeenth Day of April 1979

[SEAL]

Attest:

RUTH C. MASON
Attesting Officer

DONALD W. BANNER
Commissioner of Patents and Trademarks